United States Patent
Steiner et al.

(10) Patent No.: US 6,191,125 B1
(45) Date of Patent: Feb. 20, 2001

(54) SMALL MOLECULE PIPECOLIC ACID DERIVATIVE HAIR GROWTH COMPOSITIONS AND USES

(75) Inventors: Joseph P. Steiner, Finksburg; Gregory S. Hamilton, Catonsville, both of MD (US)

(73) Assignee: GPI NIL Holdings, Inc., Wilmington, DE (US)

(*) Notice: Under 35 U.S.C. 154(b), the term of this patent shall be extended for 0 days.

(21) Appl. No.: 09/089,373

(22) Filed: Jun. 3, 1998

Related U.S. Application Data (63) Continuation-in-part of application No. 08/869,426, filed on Jun. 4, 1997, now Pat. No. 5,945,441.

(51) Int. Cl.⁷ .................................................. A61K 31/55
(52) U.S. Cl. ......................... 514/211; 514/212; 514/880
(58) Field of Search ................................. 514/336, 211, 514/212

(56) References Cited

U.S. PATENT DOCUMENTS

| | | |
|---|---|---|
| 4,310,461 | 1/1982 | Krapcho et al. . |
| 4,374,829 | 2/1983 | Harris et al. . |
| 4,390,695 | 6/1983 | Krapcho et al. . |
| 4,438,031 | 3/1984 | Winkley et al. . |
| 4,531,964 | 7/1985 | Shimano et al. . |
| 4,574,079 | 3/1986 | Gavras et al. . |
| 4,578,474 | 3/1986 | Krapcho et al. . |
| 4,593,102 | 6/1986 | Shanklin, Jr. . |
| 4,808,573 | 2/1989 | Gold et al. . |
| 4,818,749 | 4/1989 | Gold et al. . |
| 4,996,193 | 2/1991 | Hewitt et al. . |
| 5,147,877 | 9/1992 | Goulet . |
| 5,189,042 | 2/1993 | Goulet et al. . |
| 5,192,773 | 3/1993 | Armistead et al. . |
| 5,208,241 | 5/1993 | Ok et al. . |
| 5,252,579 | 10/1993 | Skotnicki et al. . |
| 5,258,389 | 11/1993 | Goulet et al. . |
| 5,284,826 | 2/1994 | Eberle . |
| 5,284,840 | 2/1994 | Rupprecht et al. . |
| 5,284,877 | 2/1994 | Organ et al. . |
| 5,292,747 | 3/1994 | Davis et al. . |
| 5,294,603 | 3/1994 | Rinehart . |
| 5,319,098 | 6/1994 | Burbaum et al. . |
| 5,330,993 | 7/1994 | Armistead et al. . |
| 5,342,625 | 8/1994 | Hauer et al. . |
| 5,359,138 | 10/1994 | Takeuchi et al. . |
| 5,385,908 | 1/1995 | Nelson et al. . |
| 5,385,918 | 1/1995 | Connell et al. . |
| 5,414,083 | 5/1995 | Hackl et al. . |
| 5,424,454 | 6/1995 | Burbaum et al. . |
| 5,447,915 | 9/1995 | Schreiber et al. . |
| 5,457,111 | 10/1995 | Luly et al. . |
| 5,470,878 | 11/1995 | Michnick et al. . |
| 5,472,687 | 12/1995 | Proctor . |
| 5,506,228 | 4/1996 | Norton et al. . |
| 5,516,797 | 5/1996 | Armistead et al. . |
| 5,532,248 | 7/1996 | Goulet et al. . |
| 5,543,423 | 8/1996 | Zelle et al. . |
| 5,614,547 | 3/1997 | Hamilton et al. . |
| 5,620,971 | 4/1997 | Armistead et al. . |
| 5,631,017 | 5/1997 | Sharpe et al. . |
| 5,703,088 | 12/1997 | Sharpe et al. . |
| 5,714,510 | 2/1998 | Proctor . |

FOREIGN PATENT DOCUMENTS

| | | |
|---|---|---|
| 2505114 | 8/1976 | (DE) . |
| 3508251 | 9/1986 | (DE) . |
| 3931051 | 3/1991 | (DE) . |
| 4015255 | 11/1991 | (DE) . |
| 12401 | 6/1980 | (EP) . |
| 48159 | 3/1982 | (EP) . |
| 50800 | 5/1982 | (EP) . |
| 73143 | 3/1983 | (EP) . |
| 88350 | 9/1983 | (EP) . |
| 196841 | 10/1986 | (EP) . |
| 260118 | 3/1988 | (EP) . |
| 333174 | 9/1989 | (EP) . |
| 352000 | 1/1990 | (EP) . |
| 378318 | 7/1990 | (EP) . |
| 0420707 | 8/1990 | (EP) . |
| 0471135 | 8/1990 | (EP) . |
| 405994 | 1/1991 | (EP) . |
| 419049 | 3/1991 | (EP) . |
| 423714 | 4/1991 | (EP) . |
| 0443983 | 12/1991 | (EP) . |
| 0494005 | 12/1991 | (EP) . |
| 468339 | 1/1992 | (EP) . |
| 0519819 | 6/1992 | (EP) . |
| 564924 | 10/1993 | (EP) . |
| 572365 | 12/1993 | (EP) . |
| 652229 | 5/1995 | (EP) . |
| 0823419 | 8/1997 | (EP) . |
| 2247456 | 3/1992 | (GB) . |
| 04149166 | 5/1992 | (JP) . |
| 05178824 | 7/1993 | (JP) . |

(List continued on next page.)

OTHER PUBLICATIONS

Maurer, Marcus, et al., *Hair Growth Modulation by Topical Immunophilin Ligands*, Am. J. Path. 150:1433–41 (1997).

Askin, D. et al., "Effecient Degradation of FK–506 to a versatile synthetic intermediate," J. Org. Chem., 1990, 55(20), 5451–4.

Goulet, Mark T., and Boger, Joshua, "Degradative studies on the tricarbonyl containing macrolide rapamycin," Tetrahedron Lett., 1990, 31(34), 4845–8.

Jones, T. et al., "Chemistry of tricarbonyl hemiketals and application of Evans technology to the total synthesis of the immunosuppressant (–)–FK–506," J. Am. Chem. Soc., 1990, 112(8), 2998–3017.

(List continued on next page.)

*Primary Examiner*—Rebecca Cook
(74) *Attorney, Agent, or Firm*—Gary M. Nath; Todd L. Juneau; Lee C. Heiman (57) ABSTRACT

This invention relates to pharmaceutical compositions and methods for treating alopecia and promoting hair growth using pipecolic acid derivatives.

3 Claims, 4 Drawing Sheets

FOREIGN PATENT DOCUMENTS

| | | |
|---|---|---|
| WO 8800040 | 1/1988 | (WO) . |
| WO8809789 | 12/1988 | (WO) . |
| WO 8906234 | 7/1989 | (WO) . |
| WO9012805 | 11/1990 | (WO) . |
| WO9104985 | 4/1991 | (WO) . |
| WO9113088 | 9/1991 | (WO) . |
| WO9200278 | 1/1992 | (WO) . |
| WO9203472 | 3/1992 | (WO) . |
| WO9204370 | 3/1992 | (WO) . |
| WO9216501 | 10/1992 | (WO) . |
| WO9218478 | 10/1992 | (WO) . |
| WO9219593 | 11/1992 | (WO) . |
| WO9219745 | 11/1992 | (WO) . |
| wO9221313 | 12/1992 | (WO) . |
| WO9307269 | 4/1993 | (WO) . |
| WO 9314072 | 7/1993 | (WO) . |
| WO9313066 | 7/1993 | (WO) . |
| WO 9314762 | 8/1993 | (WO) . |
| WO 9318736 | 9/1993 | (WO) . |
| WO9323548 | 11/1993 | (WO) . |
| WO9325546 | 12/1993 | (WO) . |
| WO 9403476 | 2/1994 | (WO) . |
| WO9405639 | 3/1994 | (WO) . |
| WO9407858 | 4/1994 | (WO) . |
| WO9413629 | 6/1994 | (WO) . |
| WO 9502684 | 1/1995 | (WO) . |
| WO 9512398 | 5/1995 | (WO) . |
| WO9512572 | 5/1995 | (WO) . |
| WO9524385 | 9/1995 | (WO) . |
| WO 9611943 | 10/1995 | (WO) . |
| WO9526337 | 10/1995 | (WO) . |
| WO 9534303 | 12/1995 | (WO) . |
| WO9535308 | 12/1995 | (WO) . |
| WO9535367 | 12/1995 | (WO) . |
| WO9606097 | 2/1996 | (WO) . |
| WO9615101 | 5/1996 | (WO) . |
| WO9617816 | 6/1996 | (WO) . |
| WO9603318 | 10/1996 | (WO) . |
| WO9633184 | 10/1996 | (WO) . |
| WO9633187 | 10/1996 | (WO) . |
| WO9636630 | 11/1996 | (WO) . |
| WO 9641609 | 12/1996 | (WO) . |
| WO 9731898 | 9/1997 | (WO) . |
| WO 9736869 | 10/1997 | (WO) . |
| WO 9813343 | 4/1998 | (WO) . |
| WO 9822432 | 5/1998 | (WO) . |
| WO9820891 | 5/1998 | (WO) . |
| WO9820892 | 5/1998 | (WO) . |
| WO9820893 | 5/1998 | (WO) . |
| WO9824805 | 6/1998 | (WO) . |
| 9207782 | 4/1993 | (ZA) . |

OTHER PUBLICATIONS

Jones, A. et al., "A formal synthesis of FK–506. Exploration of some alternatives to macrolactamization," J. Org. Chem., 1990, 55(9), 2786–97.

Rao, A.V., et al., "Studies directed towards the synthesis of immunosuppressive agent FK–506: construction of the tricarbonyl moiety," Tetrahedron Lett., 1990, 31(10), 1439–42.

Harding, M.W., et al., "A receptor for the immunosuppressant FK506 is a cis–trans peptidyl–prolyl isomerase," Nature Lett., 1989, 341, 758–60.

Finberg, Robert W. et al., "Prevention of HIV–1 Infection and Preservation of CD4 Function by the Binding of CPFs to gp120," Science, 1990, 249, 287–91.

Goodfellow, Val S. et al., "p–Nitrophenyl 3–diazopyruvate and diazopyruvamides, a New Family of Photoactivatable Cross–Linking Bioprobes," Biochemistry, 28(15), 6346–60.

Wasserman, H.H. et al., "Synthesis of the tricarbonyl region of FK–506 through an amidosphere," J. Org. Chem., 1989, 54(12), 2785–6.

Coleman, R., and Danishefsky, S., "Degradation and manipulations of the immunosuppressant FK506: preparation of potential synthetic intermediates," Heterocycles, 1989, 28(1), 157–61.

Boulmedais, Ali et al., "Stereochemistry of Electrochemical Reduction of Optically Active α–ketoamides. II. Electroreduction of benzoylformamides derived form S–(–)–proline," Bull–Soc. Chim. Fr., 1989, (2), 185–91. (French).

Soai, Kenso et al., "Asymmetric Allylation of α–keto amides Derived from (S)–proline esters," Pept. Chem., 1986, 24, 327–330.

Egbertson, M. and Danishefsky, S., "A synthetic route to the tricarbonyl region of FK–506," J. Org. Chem., 1989, 54(1), 11–12.

Williams, D.R. and Benbow, J.W., "Synthesis of the α,β diketo amide segment of the novel immunosuppressive FK506," J. Org. Chem., 1988, 53(191), 4643–4.

Kocienski, P. et al., "A synthesis of the C(1)–C(15) segment of tsukubaenolide (FK506)," Tetrahedron Lett., 1988, 29(35), 4481–4.

Tanaka, H. et al., "Structure of FK506, a novel imunosuppressant isolated from Streptomyces," J. Am. Chem. Soc., 1987, 109(16), 5031–3.

Soai, Kenso and Ishizaki, Miyuki, "Asymmetric Synthesis of Functionalized tertiary alcohols by diastereoselective allylation of chiral α–keto amides derived from (S)–proline esters: control of stereochemistry based on saturated coordination of Lewis acid," J. Org. Chem., 1986, 51(17) 3290–5. (English).

Soai, Kenso et al., "Asymmetric synthesis of both eaniomers of α–hydroxy acids by the diastereoselective reduction of chiral α–keto amides with complex metal hydrides in the presence of a metal salt," Chem. Lett., 1986, 11, 1897–900.

Soai, Kenso and Hasegawa, Hitoshi, "Diastereoselective reduction of chiral α–ketoamides derived from (S)–proline esters with sodium borohydride. Preparation of optically active α–hydroxy acids," J. Chem. Soc., 1985, 1(4), 769–72.

Soai, Kenso and Ishizaki, Miyuki, "Diastereoselective asymmetric allylation of chiral α–keto amides with allyltrimethylsilane. Preparation of protected homoallylic alcohols," J. Chem. Soc., 1984, 15, 1016–1017.

Bender, D., et al., "Periodate oxidation of α–keto γ–lactams. Enol oxidation and β–lactam formation. Mechanism of periodate hydroxylation reactions," J. Org. Chem., 1978, 43(17), 3354–62.

Colombo, L. et al., "Enantioselective synthesis of secondary alcohols in the presence of chiral ligands," Tetrahedron, 1982, 38(17), 2725–7.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides," Synthesis, 1978, 8, 622–4. (German).

Cushman, D.W. et al., "Design of potent competitive inhibitors of angiotensin–converting enzyme. Carboxyalkanoyl and mercaptoalkanoyl amino acids," Biochemistry, 1977, 16(25), 5484–91.

Steglich, Wolfgang and Hinze, Sabine, "A rational synthesis of N–trifluroacetylamino acids," Synthesis, 1976, 8, 399–401. (German).

Marshall, J.A. et al., Convenient synthesis of dioxopiperazines via aminolysis of .alpha.–(pyruvylamino) esters, Synth. Commun., 1975, 5(3), 237–44.

Haeusler, Johannes and Schmidt, Ulrich, "Amino acids and peptides. IX. Pyruvoyl amino acids," Chem. Ber., 1974, 107(1), 145–51. (German).

Hearn, Walter R., and Worthington, Robert E., "L–Proline–N–oxalic anhydride," J. Org. Chem., 1967, 32(12), 4072–4.

Chakaraborty, Tushar K., "Studies towards the development of cyclic peptide–based analogs of macrolide immunosuppressants," Pure Appl. Chem., 1996, 68(3), 565–568.

Tugwell, Peter, "Clyclosporin in the Treatment of Rheumatoid Arthritis," J. of Autoimmunity, 1992, 5, 231–40.

Fry, Lionel, "Psoriasis: Immunopathology and Long–term treatment with Cyclosporin," J. of Autoimmunity, 1992, 5, 277–83.

Feutren, Gilles, "The Optimal use of Cyclosporin A in Autoimmune Diseases," J. of Autoimmunity, 1992, 5, 183–95.

Slee, Deborah H. et al., Selectivity in the Inhibition of HIV and FIV Protease: Inhibitory and Mechanistic Studies of Pyrrolidine–Containing α–Keto Amide and Hydroxyethylamine Core Structures, J. Am. Chem. Soc., 1995, 117(48), 1187–78.

Munoz, Benito et al., "α–Ketoamide Phe–Pro isostere as a new core structure for the inhibition of HIV protease," Bioorg. Med. Chem., 1994, 2(10), 1085–90.

Hauske, James R. et al., "Investigation of the effects of synthetic, non–cytotoxic immunophilin inhibitors on MDR," Bioorg. Med. Chem.. Lett., 1994, 4(17), 2097–102.

Mashkovskii, M.D. et al., "1–[4–(2–Hydroxy–3–tert–butylaminopropoxy)–indole–3–yl (5–acetamido–1–(S)–carboxypentyl)–DL–alanyl]–L–proline dihydrochloride, a new angiotensin–converting enzyme inhibitor with β–adrenoblocking properties," Khim.–Farm. Zh., 1993, 27(10), 16–20. (Russian).

Ranganathan, Darshan et al., "Protein Backbone Modification by Novel Cα–C Side–Chain Scission," 1994, J. Am. Chem. Soc., 116(15), 6545–57.

Baader, Ekkehard et al., "Inhibition of prolyl 4–hydroxylase by oxalyl amino acid derivatives in vitro in isolated microsomes and in embryonic chicken tissues," Biochem. J., 1994, 300(2), 525–30.

Gold, Bruce R., et al., "The Immunosuppressant FK506 Increases the Rate of Axonal Regeneration in Rat Sciatic Nerve," J. Neuroscience, 1995, 15(11):7509–7516.

Karle, Isabella L. et al., "Coformation of the oxalamide group in retro–bispeptides. Three crystal structures," Int. J. Pept. Protein Res., 1994, 43(2), 160–5.

Kaczmar, et al., Makromol. Chem., 1976, 177, 1981–9 (German).

Steiner, Joseph P. et al., "High brain densities of the immunophilin FKBP colocalized with calcineurin," Nature, 1992, 358, 584–7.

Pattenden, Gerald and Tankard, Mark, "Facile Synthesis of the tricarbonyl subunit in the immunosuppressant rapamycin," Tetrahedron Lett., 1993, 34(16), 2677–80.

Furber, M. et al., "Studies relating to the immunosuppressive activitiy of FK506," Tetrahedron Lett., 1993, 34(8), 1351–4.

Ranganathan, Darshan et al., "Oxalopeptides as core motifs for protein design," J. Chem. Soc., 1993, (1), 92–4.

Dawson, Ted M. et al., "Immunosuppressant FK506 enhances phosphorylation of nitric oxide synthase and protects against glutamate neurotoxicity," Proc. Natl. Acad. Sci. USA, 1993, 90, 9808–12.

Cunliffe, C. Jane et al., "Novel inhibitors of prolyl 4–hydroxylase. 3. Inhibition by the substrate analog N–oxaloglycine and its derivatives," J. Med. Chem., 1992, 35 (14), 2652–8.

Krit, N.A. et al., "Impact of the nature of alkyl radical on the biological activity of N–carboxyalkyl dipeptides," Khim.–Farm. Zh., 1991, 25(7), 44–6. (Russian).

Caufield, Craig E. and Musser, John H., "Macrocyclic Immunomodulators," *Annual Reports in Medicinal Chemistry*, Johns (Ed.), Academic Press, Chapter 21, 195–204, 1989.

Effenberger F. et al., "Diastereoselective addition of benzenesulfenyl chloride to 1–acryloylproline esters," Chemical Abstracts, 1989, 110:154846h.

Nakatsuka, M et al. "Total Synthesis of FK506 and an FKBP Reagent, $(C_8, C_9{-}^{13}C_2)$–FK–506," J. Am. Chem Soc., 1990, 112 (14), 5583–90..

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S. et al., "Synthesis of FK506–cyclosporin hybrid macrocycles," Bioorg. Med. Chem. Lett., 1995, 5(20), 2341–6.

Stocks, M. et al., "Macrocyclic ring closures employing the intramolecular Heck reaction," Tetrahedron Lett., 1995, 36(36), 6555–8.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Armistead, D.M. et al., "Design, synthesis and structure of non–macrocyclic inhibitors of FKBP12, the major binding protin for the immunosuppressant FK506," Acta Crystallogr. 1995, D51(4), 522–8.

Luengo, J. et al., "Structure–activity studies of rapamycin analogs: evidence that the C–7 methodoxy group is part of the effector domain and positioned at the FKBP:12–FRAP interface," Chem. Biol., 1995, 2(7), 471–81.

Furber, Mark, "FKBP–12–ligand–calceineurin interactions: analogs of SBL506," J. Am. Chem. Soc., 1995, 117(27), 7267–8.

Chakraborty, TK et al., "Design and Synthesis of a rapamycin–based high affinity binding FKBP12 ligand," Chem. Biol., 1995, 2(3), 157–61.

Wang, C.P. et al., "A high performance liquid chromatographic method for the determination of rapamycin {sirolimus} in rat serum, plasma, and blood and in monkey serum," J. Liq. Chromatogr., 1995, 18(9), 1801–8.

Baumann, K. et al., "Synthesis and oxidative cleavage of the major equilibrium products of ascomycin and Fk 506," Tetrahedron Lett., 1995, 26(13), 2231–4.

Nelson, F. et al., "A novel ring contraction of rapamycin," Tetrahedron Lett., 1994, 35(41), 7557–60.

Dawson, T.M. et al., "The immunophilins, FK506 binding and cyclophilin, are discretely localized in the brain: relationship to calcineurin," Neuroscience, 1994, 62(2), 569–80.

Cameron, Andrew et al., "Immunophilin FK506 binding protein associated with inositol 1,4,5–triphosphate receptor modulates calcium flux," Proc. Natl. Acad. Sci. USA, 1995, 92, 1784–1788.

Stocks, M. et al., "The contribution to the binding of the pyranoside sustituents in the excised binding domain of FK–506," Bioorg. Med. Chem. Lett., 1994, 4(12), 1457–60.

Steiner, J.P. et al., "Nonimmunosuppressive Ligands for Neuroimmunophilins Promote Nerve Extension In Vitro and In Vivo," Society for Neuroscience Abstracts, 1996, 22, 297.13.

Lyons, W. Ernest et al., "Neronal Regeneration Enhances the Expression of the Immunophilin FKBP–12," The Journal of Neuroscience, 1995, 15, 2985–94.

Skotnicki, Jerauld et al., "Ring expanded rapamycin derivatives," Tetrahedron Lett., 1994, 35(2), 201–2.

Skotnicki, Jerauld et al., "Synthesis of secorapamycin esters and amides," Tetrah. Lett., 1994, 35(2), 197–200.

Rao, A.V. Rama and Desibhatla, Vidyanand, "Studies directed towards the syntesis of rapamycin: stereoselective synthesis of C–1 to C–15 segment," Tetrahedron Lett., 1993, 34(44), 7111–14.

Andrus, Merrit B., "Stucture–based design of an acyclic ligand that bridges FKBP12 and calcineurin," J. Am. Chem. Soc., 1993, 115(2), 10420–1.

Luengo, Juan I. et al., "Efficient removal of pipecolinate from rapamycin and FK506 by reaction with tetrabutylammonium cyanide," Tetrahedron Lett., 1993, 34(29), 4599–602.

Steffan, Robert J. et al., "Base catalyzed degradations of rapamycin," Tetrahedron Lett., 1993, 34(23), 3699–702.

Hayward, C.M. et al., "Total Synthesis of rapamycin via a novel titanium–mediated aldol macrocyclization reaction," J. Am. Chem. Soc., 1993, 115(20), 9345–6.

Yohannes, Daniel et al., "Degradation of rapamycin: synthesis of a rapamycin–derived fragment containing the tricarbonyl and triene sectors,"Tetrahedron Lett., 1993, 34(13), 2075–8.

Luengo, J. et al., "Studies on the chemistry of rapamycin: novel transformation under Lewis–acid catalysis," Tetrahedron Lett., 1993, 34(6), 991–4.

Yohannes, Daniel et al., "Degradation of rapamycin: retrieval of major intact subunits," Tetrahedron Lett., 1992, 33(49), 7469–72.

Goulet, Mark T. and Boger, Joshua, "Degradative studies on the tricarbonyl containing macrolide rapamycin," Tetrahedron Lett., 1991, 32(45), 6454.

Goulet, Mark T. et al., "Construction of the FK–506 analog from rapamycin–derived materials," Tetrahedron Lett., 1991, 32(36), 4627–30.

Rao, A.V. Rama et al., "Studies directed towards the synthesis of immunosuppressive agent FK–506: synthesis of the entire bottom half," Tetrahedron Lett., 1991, 32(9), 1251–4.

Fisher, Matthew et al., "On the remarkable propensity for carbon–carbon bond cleavage reactions in teh C(8)–C(10) region of FK–506," J. Org. Chem., 1991, 56(8), 2900–7.

Linde, Robert G. et al., "Straightforward synthesis of 1,2, 3–tricarbonyl systems," J. Org. Chem., 1991, 56(7), 2534–8.

Hayward, C.M. et al., "An application of the Suarez reaction to the regiospecific synthesis of the $C_{28}$–$C_{42}$ segment of rapamycin," 3989–92.

Hovarth, R., et al., "An application of the Evans–Prasad 1,3–Syn diol synthesis to a stereospecific synthesis of the $C_{10}$–$C_{27}$ segment of rapamycin," Tetrahedron Lett., 1993, 34(25), 3993–3996.

Whitesell, J.K. et al., "Asymmetric Induction. Reduction, Nucleophilic Addition to, Ene Reactions of Chiral α–Ketoesters," J. Chem. Soc., Chem Commun., 1983, 802.

Ando, Takao et al., "Formation of Crossed Phenzine from the Reaction between Tetra–p–anisyl–and Tetra–p–totyl–hydrazines in Liquid Sulphur Dioxide," Chem. Comm., S. Chem. Comm., 1975, 989.

Kino, Toru et al., "FK–506, A novel immunosuppressnt isolateded from A streptomyces," J. of Antibiotics, 1987, 40(9), 1249–55.

Waldmann, Herbert, "Proline benzyl ester as chiral auxilary in Barbier–type reactions in aqueous solution," 1990, Synlett, 10, 627–8.

Steiner, Joseph P., et al., "Neurotrophic Immunophilin Liagnds Stimulate Structural and Functional Recovery in Neurodegenerative Animal Models," 1997, Proc. Natl. Aced. Sci. USA, 94:2019–2024.

Steiner, Joseph P., et al., "Neurotrophic Actions of Nonimmunosuppressive Analogues of Immunosuppressive Drugs FK506, Rapamycin and Cyclosporin A," Nat. Med. 3(4):421–428.

Birkenshaw, T.N. et al., "Synthetic FKBP12 Ligands. Design and Synthesis of Pyranose Replacements," Bioorganic & Medicinal Chemistry Letters, (1994) 4:21, 2501–2506.

Caffrey, M.V. et al., "Synthesis and Evaluation of Dual Domain Macrocyclic FKBP12 Ligands," Bioorganic & Medicinal Chemistry Letters, (1994) 4:21, 2507–2510.

Hauske, J.R. et al., "Design and Synthesis of Novel FKBP Inhibitors," J. of Medicinal Chemistry, (1992) 35, 4284–4296.

Holt, D.A. et al., "Design, Synthesis, and Kinetic Evaluation of High–Affinity FKBP Ligands and the X–ray Crystal Structures of Their Complexes with FKBP12," J. Am. Chem. Soc., (1993) 115, 9925–9938.

Holt, D.A. et al., "Structure–Activity Studies of Synthetic FKBP Ligands as Peptidyl–prolyl Isomers Inhibitors," Bioorganic & Medicinal Chemistry Letters, (1994) 4:2, 315–320.

Holt, D.A. et al., "Structure–Activity Studies of Nonmacrocyclic Rapamycin Derivatives," Bioorganic & Medicinal Chemistry Letter, (1993) 3:10, 1977–1980.

Luengo, J.I. et al., "Synthesis and Structure–Activity Relationships of Macrocyclic FKBP Ligands," Bioorganic & Medicinal Chemistry Letters, (1994) 4:2, 321–324.

Synder, S.H. et al., "Immunophilins and the Nervous System," Nature Medicine, (1995) 1:1, 32–37.

Teague, S.J. et al., "Synthesis and Study of a Non–Macrocyclic FK506 Derivative," Bioorganic & Medicinal Chemistry Letters, (1994) 4:13, 1581–1584.

Steiner, et al., Chemical Abstract, vol. 126:272710, 1997.

Teague, S.J. et al., "The Affinity of the Excised Binding Domain of FK–506 for the Immunophilin FKBP12," Bioorganic & Medicinal Chemistry Letters, (1993) 3:10, 1947–1950.

Wang, G.T. et al., "Synthesis and FKBP Binding of Small Molecule Mimics of the Tricarbonyl Region of FK506," Bioorganic and Medicinal Chemistry Letters, (1994) 4:9, 1161–1166.

Yamashita, D.S. et al., "Design, Synthesis and Evaluation of Dual Domain FKBP Ligands," Bioorganic & Medicinal Chemistry, (1994) 4:2, 325–328.

Iwabuchi, T. et al., "Effects of immunosuppressive peptidyl–prolyl cis–trans isomerase (PPIase inhibitors, cyclosporin A, FK506, ascomycin and rapamycin, on hair growth initiation in mouse: immunosuppression is not required for hair growth," J. of Deramatol. Sci., (1995) 9:1, 64–69.

Yamamoto, S. et al., "Stimulation of hair growth by topical application of FK506, a potent immunosuppressive agent," J. Invest. Dermatol, (1994) 102:2, 160–164. Abstract.

Jiang, H. et al., "Induction of anagen in telogen mouse skin by topical application of FK506, a potent immunosuppressant," J. Invest. Dermatol., (1995) 104:4, 523–525. Abstract.

SMALL MOLECULE PIPECOLIC ACID DERIVATIVE HAIR GROWTH COMPOSITIONS AND USES

This application is a continuation-in-part of U.S. patent application Ser. No. 08/869,426, filed on Jun. 4, 1997, now U.S. Pat. No. 5,945,441, the entire contents of which are herein incorporated by reference.

BACKGROUND OF THE INVENTION

1. Field of Invention

This invention relates to pharmaceutical compositions and methods for treating alopecia and promoting hair growth using low molecular weight, small molecule pipecolic acid derivatives.

2. Description of Related Art

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., J. Invest. Dermatol., 1994, 102, 160–164; Jiang et al., J. Invest. Dermatol. 1995, 104, 523–525) and cyclosporin (Iwabuchi et al., J. Dermatol. Sci. 1995, 9, 64–69) stimulates hair growth in a dose-dependent manner. One form of hair loss, alopecia areata, is known to be associated with autoimmune activities; hence, topically administered immunomodulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressant, small molecule compounds which are useful as hair revitalizing compounds.

Hamilton and Steiner disclose in U.S. Pat. No. 5,614,547 novel pyrrolidine carboxylate compounds which bind to the immunophilin FKBP12 and stimulate nerve growth, but which lack immunosuppressive effects. Unexpectedly, it has been discovered that these non-immunosuppressant compounds promote hair growth with an efficacy similar to FK506. Yet their novel small molecule structure and non-immunosuppressive properties differentiate them from FK506 and related immunosuppressive compounds found in the prior art.

SUMMARY OF THE INVENTION

The present invention relates to a method for treating alopecia or promoting hair growth in an animal, which comprises administering to said animal an effective amount of a low molecular weight, small molecule pipecolic acid derivative.

The present invention further relates to a pharmaceutical composition which comprises:

(i) an effective amount of a pipecolic acid derivative for treating alopecia or promoting hair growth in an animal; and (ii) a pharmaceutically acceptable carrier.

The pipecolic acid derivatives used in the inventive methods and pharmaceutical compositions include immunosuppressive and non-immunosuppressive compounds having an affinity for FKBP-type immunophilins, particularly FKBP12. Non-immunosuppressive compounds, as their name suggests, do not exert any significant immunosuppressive activity.

BRIEF DESCRIPTION OF THE DRAWINGS

FIG. 1 shows that less than 3% of the shaved area is covered with new hair growth when the vehicle (control) is administered.

FIG. 2 shows that 90% of the shaved area is covered with new hair growth when GPI 1044 is administered.

FIG. 4 demonstrates the remarkable early hair growth promoted by neuroimmunophilin FKBP ligands.

DETAILED DESCRIPTION OF THE INVENTION

Definitions

"Alopecia" refers to deficient hair growth and partial or complete loss of hair, including without limitation androgenic alopecia (male pattern baldness), toxic alopecia, alopecia senilis, alopecia areata, alopecia pelada and tricho- tillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"GPI 1044" refers to Compound 4.

"GPI 1102" refers to 4-phenyl-1-(3-phenylpropyl) butyl 1- (3,3-dimethyl-2-oxopentanoyl) -2-piperidinecarboxylate.

"GPI 1116" refers to 1-phenethyl-3-phenylpropyl 1-(3,3-dimethyl-2-oxopentanoyl)-2-piperidinecarboxylate.

"GPI 1206" refers to a compound of formula

GPI 1206

"Isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Pharmaceutically acceptable salt, ester, or solvate" refers to a salt, ester, or solvate of a subject compound which possesses the desired is pharmacological activity and which is neither biologically nor otherwise undesirable. A salt, ester, or solvate can be formed with inorganic acids such as acetate, adipate, alginate, aspartate, benzoate, benzenesulfonate, bisulfate, butyrate, citrate, camphorate, camphorsulfonate, cyclopentanepropionate, digluconate, dodecyl sulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, naphthylate, 2-naphthalenesulfonate, nicotinate, oxalate, sulfate, thiocyanate, tosylate and undecanoate. Examples of base salts, esters, or solvates include ammonium salts; alkali metal salts, such as sodium and potassium salts; alkaline earth metal salts, such as calcium and magnesium salts; salts with organic bases, such as dicyclohexylamine salts; N-methyl-D-glucamine; and salts with amino acids, such as arginine, lysine, and so forth. Also, the basic nitrogen-containing groups can be quarternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; aralkyl halides, such as benzyl and phenethyl bromides; and others. Water or oil-soluble or dispersible products are thereby obtained.

"Pilar cycle" refers to the life cycle of hair follicles, and includes three phases:
(1) the anagen phase, the period of active hair growth which, insofar as scalp hair is concerned, lasts about three to five years;
(2) the catagen phase, the period when growth stops and the follicle atrophies which, insofar as scalp hair is concerned, lasts about one to two weeks; and
(3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Treating alopecia" refers to:
(i) preventing alopecia in an animal which may be predisposed to alopecia; and/or
(ii) inhibiting, retarding or reducing alopecia; and/or
(iii) promoting hair growth; and/or
(iv) prolonging the anagen phase of the hair cycle; and/or
(v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

METHODS OF THE PRESENT INVENTION

The present invention relates to a method for treating alopecia or promoting hair growth in an animal, which comprises administering to said animal an effective amount of a pipecolic acid derivative.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

Pharmaceutical Compositions of the Present Invention

The present invention also relates to a pharmaceutical composition comprising:
(i) an effective amount of a pipecolic acid derivative for treating alopecia or promoting hair growth in an animal; and
(ii) a pharmaceutically acceptable carrier.

PIPECOLIC ACID DERIVATIVES

The pipecolic acid derivatives used in the methods and pharmaceutical compositions of the present invention are low molecular weight, small molecule compounds having an affinity for FKBP-type immunophilins, such as FKBP12. When a pipecolic acid derivative binds to an FKBP-type immunophilin, it has been found to inhibit the prolyl-peptidyl cis-trans isomerase, or rotamase, activity of the binding protein. Unexpectedly, the compounds have also been found to stimulate hair growth. These rotamase inhibiting compounds may be immunosuppressive or non-immunosuppressive. Examples of useful compounds are set forth below.

FORMULA I

An exemplary pipecolic acid derivative is a compound of formula I or a pharmaceutically acceptable salt, ester, or solvate thereof, wherein:

m is 0–3;

A is $CH_2$, O, NH, or N—($C_1$–$C_4$ alkyl);

B and D are independently Ar, $C_5$–$C_7$ cycloalkyl substituted $C_1$–$C_6$ straight or branched chain alkyl or $C_2$–$C_6$ straight or branched chain alkenyl, $C_5$–$C_7$ cycloalkenyl substituted $C_1$–$C_6$ straight or branched chain alkyl or $C_2$–$C_6$ straight or branched chain alkenyl, or Ar substituted $C_1$–$C_6$ straight or branched chain alkyl or $C_2$–$C_6$ straight or branched chain alkenyl, wherein in each case, one or two carbon atom(s) of said alkyl or alkenyl may be substituted with one or two heteroatom(s) independently selected from the group consisting of oxygen, sulfur, So, and $SO_2$ in chemically reasonable substitution patterns, or wherein Q is hydrogen, $C_1$–$C_6$ straight or branched chain alkyl, or $C_2$–$C_6$ straight or branched chain alkenyl; and T is Ar or $C_5$–$C_7$ cycloalkyl substituted at positions 3 and 4 with substituents independently selected from the group consisting of hydrogen, hydroxy, O—($C_1$–$C_4$ alkyl), O—($C_2$–$C_4$ alkenyl), and carbonyl;

Ar is selected from the group consisting of 1-napthyl, 2-napthyl, 2-furyl, 3-furyl, 2-thienyl, 3-thienyl, 2-pyridyl, 3-pyridyl, 4-pyridyl and phenyl, monocyclic and bicyclic heterocyclic ring systems with individual ring sizes being 5 or 6 which contain in either or both rings a total of 1–4 heteroatom(s) independently selected from the group consisting of oxygen, nitrogen and sulfur; wherein Ar contains 1–3 substituent(s) independently selected from the group consisting of hydrogen, halo, hydroxy, hydroxymethyl, nitro, $CF_3$, trifluoromethoxy, $C_1$–$C_6$ straight or branched chain alkyl, $C_2$–$C_6$ straight or branched chain alkenyl, O—($C_1$–$C_4$ straight or branched chain alkyl), O—($C_2$–$C_4$ straight or branched chain alkenyl), O-benzyl, O-phenyl, amino, 1,2-methylenedioxy, carbonyl, and phenyl;

L is either hydrogen or U; M is either oxygen or CH—U, provided that if L is hydrogen, then M is CH—U, or if M is oxygen then L is U;

U is hydrogen, O—($C_1$–$C_4$ straight or branched chain alkyl), O—($C_2$–$C_4$ straight or branched chain alkenyl), $C_1$–$C_6$ straight or branched chain alkyl, $C_2$–$C_6$ straight is or branched chain alkenyl, $C_5$–$C_7$ cycloalkyl, $C_5$–$C_7$ cycloalkenyl substituted with $C_1$–$C_4$ straight or branched chain alkyl or $C_2$–$C_4$ straight or branched chain alkenyl, ($C_1$–$C_4$ alkyl or $C_2$–$C_4$ alkenyl)-Ar, or Ar;

J is hydrogen, $C_1$ or $C_2$ alkyl, or benzyl; K is $C_1$–$C_4$ straight or branched chain alkyl, benzyl or cyclohexylmethyl; or J and K are taken together to form a 5–7 membered heterocyclic ring which is substituted with oxygen, sulfur, SO, or $SO_2$; and said pipecolic acid derivative has an affinity for FKBP-type immunophilins.

Representative species of Formula I are presented in Table I.

TABLE I

| Compound | n | m | B | D | L |
|---|---|---|---|---|---|
| 1 | 2 | 0 | 3-Phenyl-propyl | 3-(3-Pyridyl)-propyl | Phenyl |
| 2 | 2 | 0 | 3-Phenyl-propyl | 3-(2-Pyridyl)-propyl | Phenyl |
| 3 | 2 | 0 | 3-Phenyl-propyl | 2-(4-Methoxy-phenyl)ethyl | Phenyl |
| 4 | 2 | 0 | 3-Phenyl-propyl | 3-Phenylpropyl | Phenyl |
| 5 | 2 | 0 | 3-Phenyl-propyl | 3-Phenylpropyl | 3,4,5-Trimethoxyphenyl |
| 6 | 2 | 0 | 3-Phenyl-propyl | 2-(3-Pyridyl)-propyl | 3,4,5-Trimethoxyphenyl |
| 7 | 2 | 0 | 3-Phenyl-propyl | 3-(2-Pyridyl)-propyl | 3,4,5-Trimethoxyphenyl |
| 8 | 2 | 0 | 3-Phenyl-propyl | 3-(4-Methoxy-phenyl)propyl | 3,4,5-Trimethoxyphenyl |
| 9 | 2 | 0 | 3-Phenyl-propyl | 3-(3-Pyridyl)-propyl | 3-Isopropoxy-phenyl |

FORMULA II

U.S. Pat. No. 5,330,993, incorporated herein by reference, discloses an exemplary pipecolic acid derivative of Formula II

II or a pharmaceutically acceptable salt, ester, or solvate thereof, wherein:

A is O, NH, or N—(C$_1$–C$_4$ alkyl);

B is hydrogen, CHL—Ar, C$_1$–C$_6$ straight or branched chain alkyl, C$_2$–C$_6$ straight or branched chain alkenyl, C$_5$–C$_7$ cycloalkyl, C$_5$–C$_7$ cycloalkenyl, Ar substituted C$_1$–C$_6$ alkyl or C$_2$–C$_6$ alkenyl, or wherein L and Q are independently hydrogen, C$_1$–C$_6$ straight or branched chain alkyl, or C$_2$–C$_6$ straight or branched chain alkenyl; and T is Ar or C$_5$–C$_7$ cyclohexyl substituted at positions 3 and 4 with substituents independently selected from the group consisting of hydrogen, hydroxy, O—(C$_1$–C$_4$ alkyl), O—(C$_2$–C$_4$ alkenyl), and carbonyl;

Ar is selected from the group consisting of 1-napthyl, 2-napthyl, 2-furyl, 3-furyl, 2-thienyl, 2-pyridyl, 3-pyridyl, 4-pyridyl and phenyl having 1–3 substituent(s) independently selected from the group consisting of hydrogen, halo, hydroxy, nitro, CF$_3$, C$_1$–C$_6$ straight or branched chain alkyl, C$_2$–C$_6$ straight or branched chain alkenyl, O—(C$_1$–C$_4$ straight or branched chain alkyl), O—(C$_2$–C$_4$ straight or branched chain alkenyl), O-benzyl, O-phenyl, amino, and phenyl.

D is hydrogen or U; E is oxygen or CH—U, provided that if D is hydrogen, then E is CH—U, or if E is oxygen, then D is U;

U is hydrogen, O—(C$_1$–C$_4$ straight or branched chain alkyl), O—(C$_2$–C$_4$ straight or branched chain alkenyl), C$_1$–C$_6$ straight or branched chain alkyl, C$_2$–C$_6$ straight or branched chain alkenyl, C$_5$–C$_7$-cycloalkyl, C$_5$–C$_7$ cycloalkenyl substituted with C$_1$–C$_4$ straight or branched chain alkyl or C$_2$–C$_4$ straight or branched chain alkenyl, 2-indolyl, 3-indolyl, (C$_1$–C$_4$ alkyl or C$_2$–C$_4$ alkenyl)-Ar, or Ar;

J is hydrogen, C$_1$ or C$_2$ alkyl, or benzyl; K is C$_1$–C$_4$ straight or branched chain alkyl, benzyl or cyclohexylethyl; or J and K are taken together to form a 5–7 membered heterocyclic ring which is substituted with oxygen, sulfur, SO, or SO$_2$.

FORMULA III

A preferred pipecolic acid derivative is a compound of Formula III

III or a pharmaceutically acceptable salt, ester, or solvate thereof, wherein:

n is 2;

D is phenyl, methoxy, 2-furyl, or 3,4,5-trimethoxyphenyl; and

B is benzyl, 3-phenylpropyl, 4-(4-methoxyphenyl)butyl, 4-phenylbutyl, phenethyl, 3-cyclohexylpropyl, 4-cyclohexylbutyl, 3-cyclopentylpropyl, 4-cyclohexylbutyl, 3-phenoxybenzyl, 3-(3-indolyl)propyl, or 4-(4-methoxyphenyl)butyl;

provided that:

when D is phenyl, then B is benzyl, 3-phenylpropyl, 4-(4-methoxyphenyl)butyl, 4-phenylbutyl, phenethyl, or 4-cyclohexylbutyl;

when D is methoxy, B is benzyl, 4-cyclohexylbutyl, 3-cyclohexylpropyl, or 3-cyclopentylpropyl;

when D is 2-furyl, then B is benzyl; and when D is 3,4,5-trimethoxyphenyl, then B is 4-cyclohexylbutyl, 3-phenoxybenzyl, 4-phenylbutyl, 3-(3-indolyl) propyl, or 4-(4-methoxyphenyl) butyl.

Representative species of Formula III are presented in Table II.

IV

FORMULA IV

The pipecolic acid derivative may also be a compound of formula IV

IV or a pharmaceutically acceptable salt, ester, or solvate thereof, wherein:

V is C, N, or S;

J and K, taken together with V and the carbon atom to which they are respectively attached, form a 5–7 membered saturated or unsaturated heterocyclic ring containing, in addition to V, one or more heteroatom(s) selected from the group consisting of O, S, SO, $SO_2$, N, NH, and NR;

R is either $C_1$–$C_9$ straight or branched chain alkyl, $C_2$–$C_9$ straight or branched chain alkenyl, $C_3$–$C_9$ cycloakyl, $C_5$–$C_7$ cycloalkenyl, or $Ar_1$, wherein R is either unsubstituted of substituted with one or more substituent(s) independently selected from the group consisting of halo, haloalkyl, carbonyl, carboxy, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, thioalkyl, alkylthio, sulfhydryl, amino, alkylamino, aminoalkyl, aminocarboxyl, and $Ar_2$;

$Ar_1$ and $Ar_2$ are independently an alicyclic or aromatic, mono-, bi- or tricyclic, carbo- or heterocyclic ring; wherein the individual ring size is 5–8 members; wherein said heterocyclic ring contains 1–6 heteroatom(s) independently selected from the group consisting of O, N, and S;

A, B, D, L, M, and m are as defined in Formula I above; and said pipecolic acid derivative has an affinity for FKBP-type immunophilins.

All the compounds of Formulas I–IV possess asymmetric centers and thus can be produced as mixtures of stereoisomers or as individual R- and S-stereoisomers. The individual stereoisomers may be obtained by using an optically active starting material, by resolving a racemic or non-racemic mixture of an intermediate at some appropriate stage of the synthesis, or by resolving the compounds of Formulas I–IV. It is understood that the compounds of Formulas I–IV encompass individual stereoisomers as well as mixtures (racemic and non-racemic) of stereoisomers. Preferably, S-stereoisomers are used in the pharmaceutical compositions and methods of the present invention.

Affinity for FKBP12

The compounds used in the inventive methods and pharmaceutical compositions have an affinity for the FK506 binding protein, particularly FKBP12. The inhibition of the prolyl peptidyl cis-trans isomerase activity of FKBP may be measured as an indicator of this affinity.

K. Test Procedure

Inhibition of the peptidyl-prolyl isomerase (rotamase) activity of the compounds used in the inventive methods and pharmaceutical compositions can be evaluated by known methods described in the literature (Harding et al., *Nature*, 1989, 341:758–760; Holt et al. *J. Am. Chem. Soc.*, 115:9923–9938). These values are obtained as apparent $K_i$'s and are presented for representative compounds in TABLE III.

The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate.

The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

TABLE III

In Vitro Test Results - Formulas I–III

| Compound | $K_i$ ($\mu M$) |
|---|---|
| 10 | 1.5 |
| 13 | 0.35 |
| 14 | 1.1 |
| 15 | 0.4 |
| 16 | 80 |
| 17 | 6 |
| 18 | 20 |
| 19 | 35 |
| 20 | 3 |
| 21 | 0.04 |
| 22 | 0.018 |
| 23 | 0.019 |
| 24 | 0.017 |
| 25 | 0.013 |

Route of Administration

To effectively treat alopecia or promote hair growth, the compounds used in the inventive methods and pharmaceutical compositions must readily affect the targeted areas. For these purposes, the compounds are preferably administered topically to the skin.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Other routes of administration known in the pharmaceutical art are also contemplated by this invention.

Dosage

Dosage levels on the order of about 0.1 mg to about 10,000 mg of the active ingredient compound are useful in the treatment of the above conditions, with preferred levels of about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The compounds can be administered with other hair revitalizing agents. Specific dose levels for the other hair revitalizing agents will depend upon the factors previously stated and the effectiveness of the drug combination.

EXAMPLES

The following examples are illustrative of the present invention and are not intended to be limitations thereon. Unless otherwise indicated, all percentages are based upon 100% by weight of the final composition.

Example 1

In Vivo Hair Generation Tests With C57 Black 6 Mice

Figure 1:
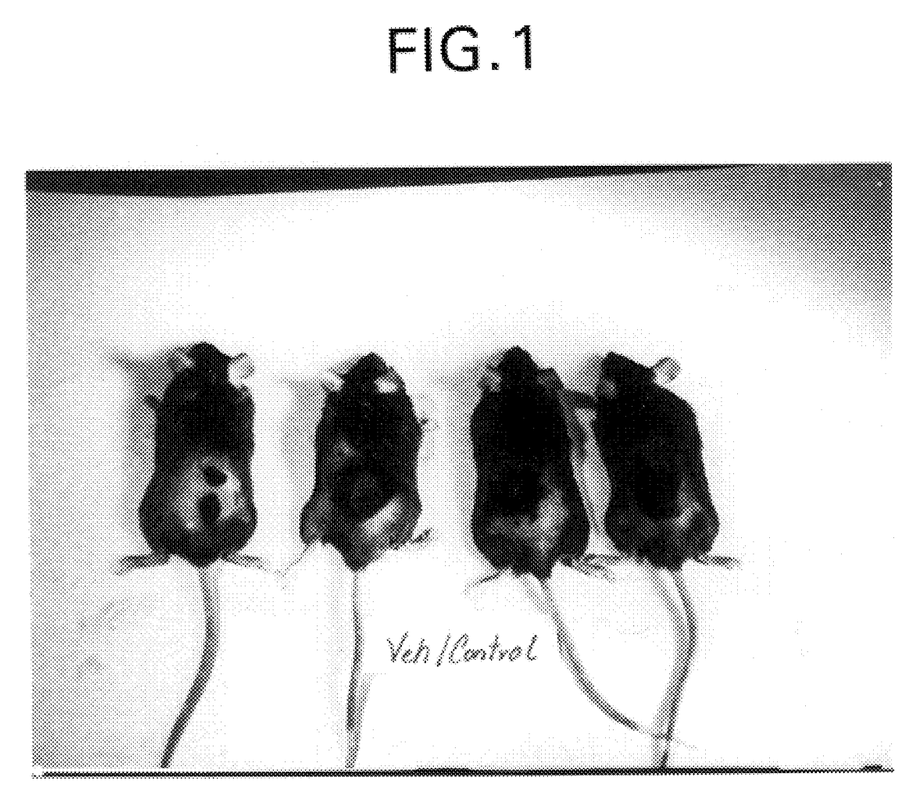
FIG. 1 is a photograph of mice treated with a vehicle after six weeks.
Figure 2:
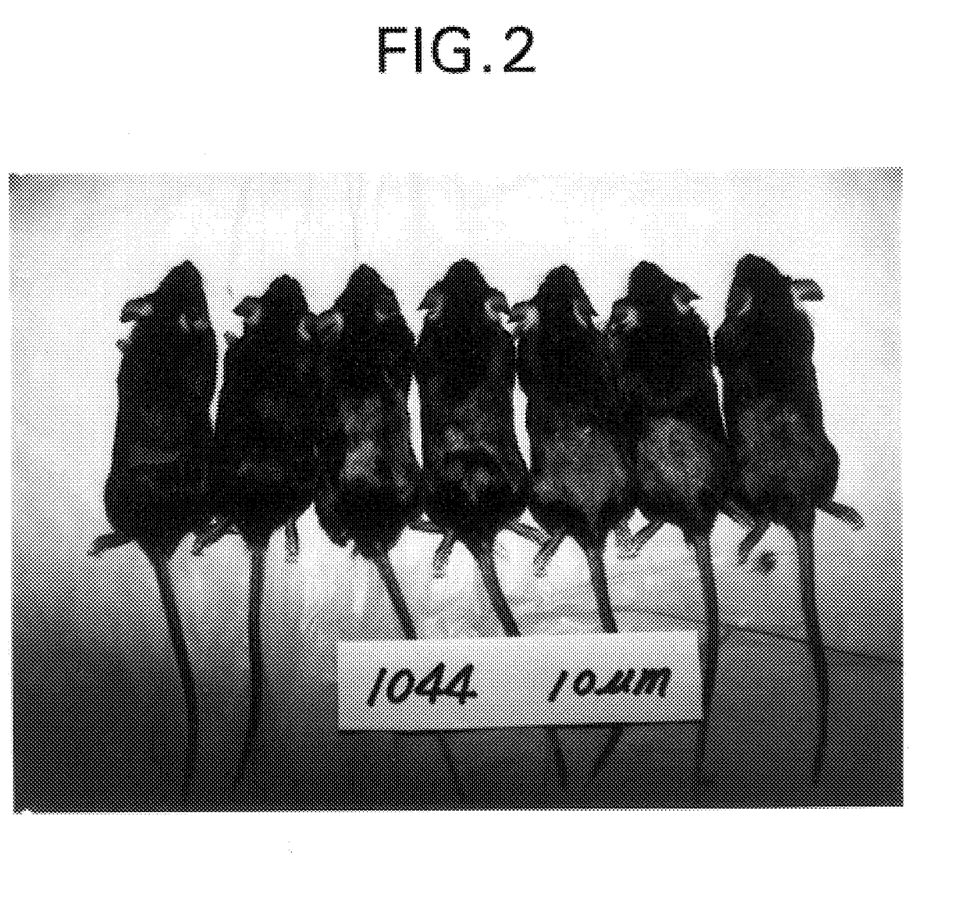
FIG. 2 is a photograph of mice treated with 10 $\mu$M of GPI 1044 after six weeks.

Experiment A: C57 black 6 mice were used to demonstrate the hair revitalizing properties of pipecolic acid derivative GPI 1044 (compound 4), as well as related pipecolic acid derivative neuroimmunophilin FKBP ligands GPI 1102 and GPI 1116. C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIGS. 1 and 2, four animals were treated by topical administration with 20% propylene glycol vehicle (FIG. 1), and seven animals were treated by topical administration with 10 $\mu$M GPI 1044 (FIG. 2). The animals were treated with vehicle or GPI 1044 every 48 hours (3 applications total over the course of 5 days) and the hair growth was allowed to proceed for 6 weeks. Hair growth was quantitated by the percent of shaved area covered by new hair growth during this time period.

Figure 3:
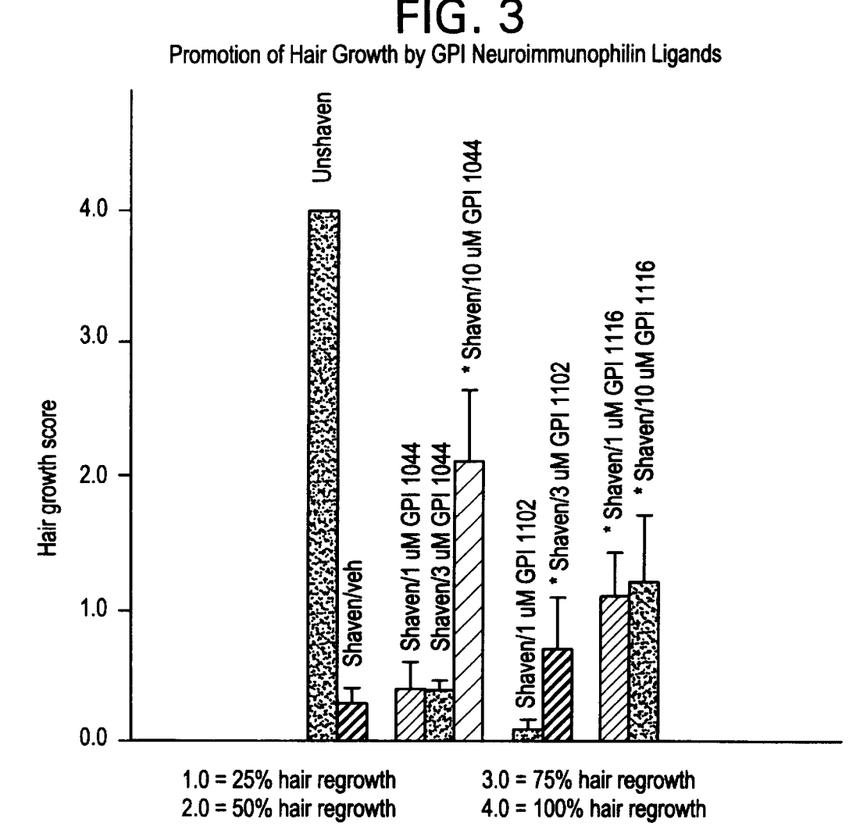
FIG. 3 is a bar graph plotting the hair growth scores of unshaven animals and shaven animals treated with a vehicle, GPI 1044 (1 $\mu$M, 3 $\mu$M and 10 $\mu$M), and related pipecolic acid derivative neuroimmunophilin FKBP ligands GPI 1116 (1 $\mu$M and 10 $\mu$M) and GPI 1102 (1 $\mu$M and 3 $\mu$M).

FIG. 1 shows that animals treated with vehicle exhibited only a small amount of hair growth in patches or tufts, with less than 3% of the shaved area covered with new growth. In contrast, FIG. 2 shows that animals treated with 10 $\mu$M GPI 1044 exhibited dramatic hair growth, covering as much as 50% of the shaved area in some animals. FIG. 3 compares the hair growth score of unshaven animals with the hair growth scores of shaven animals treated with a vehicle and GPI 1044 (1 $\mu$M, 3 $\mu$M and 10 $\mu$M), as well as related neuroimmunophilin FKBP ligands GPI 1116 (1 $\mu$M and 10 $\mu$M) and GPI 1102 (1 $\mu$M and 3 $\mu$M).

Experiment B: C57 Black 6 mice were used to demonstrate the hair revitalizing properties of neuroimmunophilin FKBP ligands. C57 Black 6 mice, 55 to 75 days old, had an area of about 2 inches by 2 inches on their hindquarters shaved to remove all existing hair. Care was taken not to nick or cause abrasion to the underlying dermal layers. The animals were in a anagen growth phase when shaved. Five animals per group were treated by topical administration with a vehicle, FK506, or a neuroimmunophilin FKBP ligand (GPI 1116 or 1206) at a concentration of one micromole per milliliter to the shaved area. The animals were treated three times per week, and hair growth was evaluated 14 days after initiation of treatment. Hair growth was quantitated by the percent of shaved area covered by new hair growth, as scored by a blinded observer, on a scale of 0 (no growth) to five (complete hair regrowth in shaved area).

Figure 4:
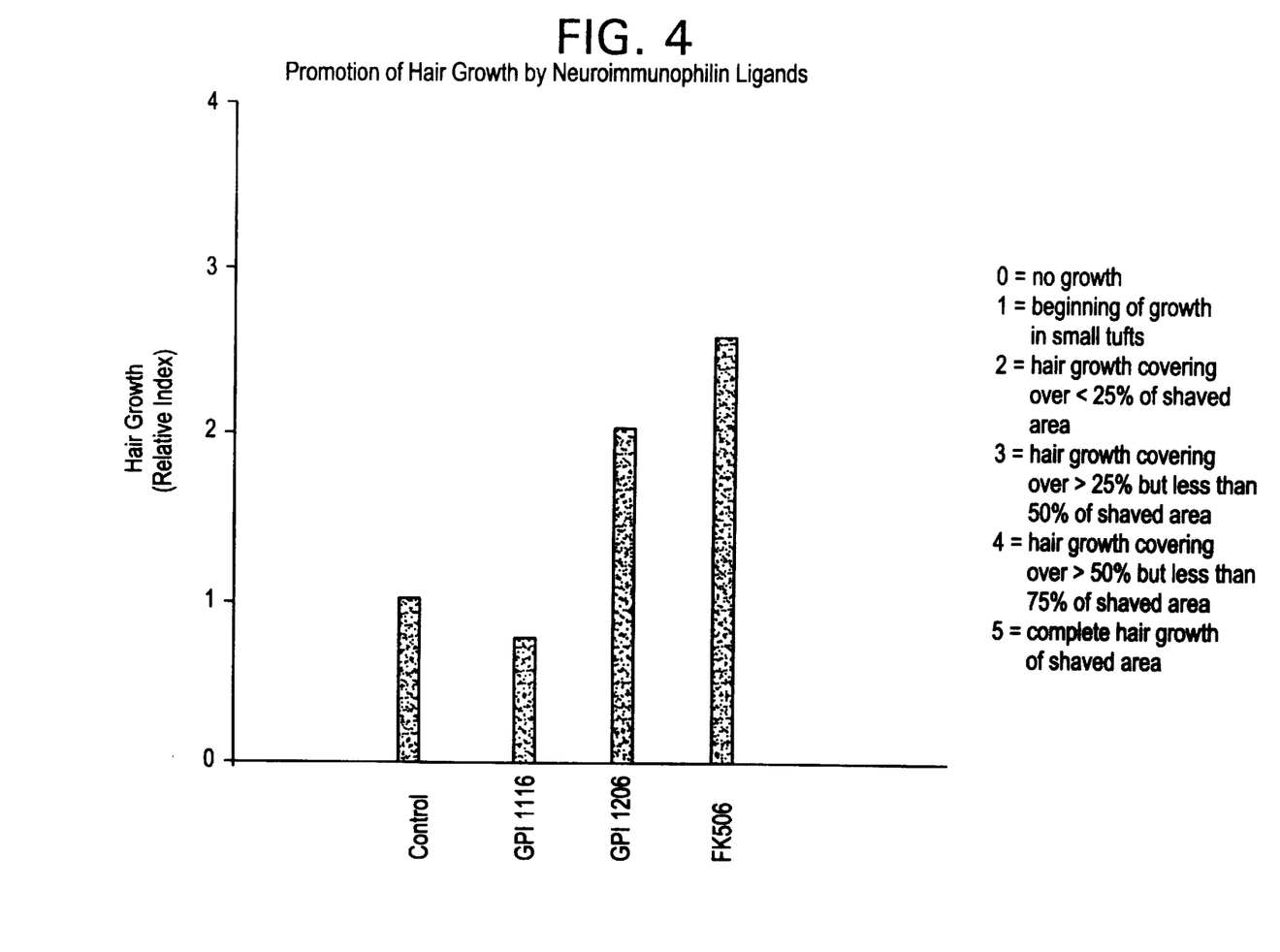
FIG. 4 is a bar graph depicting the relative hair growth indices for C57 Black 6 mice treated with a vehicle, FK506, and related neuroimmunophilin FKBP ligands 14 days after treatment with each identified compound.

FIG. 4 shows that after 14 days, the animals treated with vehicle exhibited the beginning of growth in small tufts. In contrast, animals treated with one of the low molecular weight, small molecule, neuroimmunophilin FKBP ligands exhibited dramatic hair growth.

Example 2

A lotion comprising the following composition may be prepared.

|  | (%) |
| --- | --- |
| 95% Ethanol | 80.0 |
| a pipecolic acid derivative as defined above | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added a pipecolic acid derivative, α-tocopherol acetate, ethylene oxide (40 mole) adducts of hardened castor oil, perfume and a dye. The resulting mixture is stirred and dissolved, and purified water is added to the mixture to obtain a transparent liquid lotion.

5 ml of the lotion may be applied once or twice per day to a site having marked baldness or alopecia.

Example 3

A lotion comprising the following composition shown may be prepared.

|  | (%) |
| --- | --- |
| 95% Ethanol | 80.0 |
| a pipecolic acid derivative as defined above | 0.005 |
| Hinokitol | 0.01 |
| Ethylene oxide (40 mole) adducts of hardened castor oil | 0.5 |
| Purified water | 19.0 |
| Perfume and dye | q.s. |

Into 95% ethanol are added a pipecolic acid derivative, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 4

An emulsion may be prepared from A phase and B phase having the following compositions.

| (A phase) | (%) |
| --- | --- |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitan monooleate | 1.0 |
| a pipecolic acid derivative as defined above | 0.01 |
| (B phase) | (%) |
| Glycerine | 10.0 |
| Purified water | 69.0 |
| Perfume, dye, and preservative | q.s. |

The A phase and the B phase are respectively heated and melted and maintained at 80° c. Both phases are then mixed and cooled under stirring to normal temperature to obtain an emulsion.

The emulsion may be applied by spraying once to four times per day to a site having marked baldness or alopecia.

Example 5

A cream may be prepared from A phase and B phase having the following compositions.

| (A Phase) | (%) |
| --- | --- |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) | (%) |
| a pipecolic acid derivative as defined above | 0.8 |
| Glycerine | 7.0 |
| Dipropylene glycol | 20.0 |
| Polyethylene glycol 4000 | 5.0 |
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 6

A liquid comprising the following composition may be prepared.

| | (%) |
| --- | --- |
| Polyoxyethylene butyl ether | 20.0 |
| Ethanol | 50.0 |
| a pipecolic acid derivative as defined above | 0.001 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, a pipecolic acid derivative, and perfume. The resulting mixture is stirred, and purified water is added to the mixture to obtain a liquid.

The liquid may be applied once to 4 times per day to a site having marked baldness or alopecia.

Example 7

A shampoo comprising the following composition may be prepared.

| | (%) |
| --- | --- |
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| a pipecolic acid derivative as defined above | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethyl-aminoacetate. Then a mixture obtained by adding 5.0 g of a pipecolic acid derivative, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 8

A patient is suffering from alopecia senilis. A pipecolic acid derivative, or a pharmaceutical composition comprising the same, may be administered to the patient. Increased hair growth is expected to occur following treatment.

Example 9

A patient is suffering from male pattern alopecia. A pipecolic acid derivative, or a pharmaceutical composition comprising the same, may be administered to the patient. Increased hair growth is expected to occur following treatment.

Example 10

A patient is suffering from alopecia areata. A pipecolic acid derivative, or a pharmaceutical composition comprising the same, may be administered to the patient. Increased hair growth is expected to occur following treatment.

Example 11

A patient is suffering from hair loss caused by skin lesions. A pipecolic acid derivative, or a pharmaceutical composition comprising the same, may be administered to the patient. Increased hair growth is expected to occur following treatment.

Example 12

A patient is suffering from hair loss caused by tumors. A pipecolic acid derivative, or a pharmaceutical composition comprising the same, may be administered to the patient. Increased hair growth is expected to occur following treatment.

Example 13

A patient is suffering from hair loss caused by a systematic disorder, such as a nutritional disorder or an internal secretion disorder. A pipecolic acid derivative, or a pharmaceutical composition comprising the same, may be administered to the patient. Increased hair growth is expected to occur following treatment.

Example 14

A patient is suffering from hair loss caused by chemotherapy. A pipecolic acid derivative, or a pharmaceutical composition comprising the same, may be administered to the patient. Increased hair growth is expected to occur following treatment.

Example 15

A patient is suffering from hair loss caused by radiation. A pipecolic acid derivative, or a pharmaceutical composition comprising the same, may be administered to the patient. Increased hair growth is expected to occur following treatment.

The invention being thus described, it will be obvious that the same may be varied in many ways. Such variations are not to be regarded as a departure from the spirit and scope of the invention and all such modifications are intended to be included within the scope of the following claims.

We claim:

1. A method for treating alopecia or promoting hair growth in an animal in need thereof, which comprises administering to said animal an effective amount of a compound of formula I or a pharmaceutically acceptable salt, ester, or solvate thereof, wherein:

A is O, NH, or N—($C_1$–$C_4$ alkyl);

B and D are independently Ar, $C_5$–$C_7$ cycloalkyl substituted $C_1$–$C_6$ straight or branched chain alkyl or $C_2$–$C_6$ straight or branched chain alkenyl, $C_5$–$C_7$ cycloalkenyl substituted $C_1$–$C_6$ straight or branched chain alkyl or $C_2$–$C_6$ straight or branched chain alkenyl, or Ar substituted $C_1$–$C_6$ straight or branched chain alkyl or $C_2$–$C_6$ straight or branched chain alkenyl, wherein in each case, one or two carbon atom(s) of said alkyl or alkenyl is/are optionally substituted with one or two heteroatom(s) independently selected from the group consisting of oxygen, sulfur, SO, and $SO_2$, or wherein Q is hydrogen, $C_1$–$C_6$ straight or branched chain alkyl or $C_2$–$C_6$ straight or branched chain alkenyl; and T is Ar or $C_5$–$C_7$ cycloalkyl substituted at positions 3 and 4 with substituents independently selected from the group consisting of hydrogen, hydroxy, O—($C_1$–$C_4$ alkyl), O-($C_2$–$C_4$ alkenyl), and carbonyl;

Ar is selected from the group consisting of 1-napthyl, 2-napthyl, 2-furyl, 3-furyl, 2-thienyl, 3-thienyl, 2-pyridyl, 3-pyridyl, 4-pyridyl and phenyl, monocyclic and bicyclic heterocyclic ring systems with individual ring sizes being 5 or 6 which have in either or both rings a total of 1–4 heteroatoms independently selected from oxygen, nitrogen and sulfur; wherein Ar has 1–3 substituent(s) independently selected from the group consisting of hydrogen, halo, hydroxy, hydroxymethyl, nitro, $CF_3$, trifluoromethoxy, $C_1$–$C_6$ straight or branched chain alkyl, $C_2$–$C_6$ straight or branched chain alkenyl, O-($C_1$–$C_4$ straight or branched chain alkyl), O—($C_2$–$C_4$ straight or branched chain alkenyl), O-benzyl, O-phenyl, amino, 1,2-methylenedioxy, carbonyl, and phenyl;

L is either hydrogen or U; M is either oxygen or CH—U, provided that if L is hydrogen, then M is CH—U, or if M is oxygen then L is U;

U is hydrogen, O—($C_1$–$C_4$ straight or branched chain alkyl), O-($C_2$–$C_4$ straight or branched chain alkenyl), $C_1$–$C_6$ straight or branched chain alkyl, $C_2$–$C_6$ straight or branched chain alkenyl, $C_5$–$C_7$ cycloalkyl, $C_5$–$C_7$ cycloalkenyl substituted with $C_1$–$C_4$ straight or branched chain alkyl or $C_2$–$C_4$ straight or branched chain alkenyl, ($C_1$–$C_4$ alkyl or $C_2$–$C_4$ alkenyl)-Ar, or Ar;

J is hydrogen, $C_1$ or $C_2$ alkyl, or benzyl; K is $C_1$–$C_4$ straight or branched chain alkyl, benzyl or cyclohexylmethyl; or J and K are taken together to form a 7 membered heterocyclic ring which is substituted with oxygen, sulfur, SO, or $SO_2$;

m is 0–3; and said compound has an affinity for FKBP-type immunophilins.

2. A method for treating alopecia or promoting hair growth in an animal in need thereof, which comprises administering to said animal an effective amount of a compound of formula II or a pharmaceutically acceptable salt, ester, or solvate thereof, wherein:

A is O, NH, or N—($C_1$–$C_4$ alkyl);

B is hydrogen, CHL—Ar, $C_1$–$C_6$ straight or branched chain alkyl, $C_2$-$C_6$ straight or branched chain alkenyl, $C_5$–$C_7$ cycloalkyl, $C_5$–$C_7$ cycloalkenyl, Ar substituted $C_1$–$C_6$ alkyl or $C_2$–$C_6$ alkenyl, or wherein L and Q are independently hydrogen, $C_1$–$C_6$ straight or branched chain alkyl, or $C_2$–$C_6$ straight or branched chain alkenyl; and T is Ar or $C_5$–$C_7$ cyclohexyl substituted at positions 3 and 4 with substituents independently selected from the group consisting of hydrogen, hydroxy, O—($C_1$–$C_4$ alkyl), O—($C_2$–$C_4$ alkenyl), and carbonyl;

Ar is selected from the group consisting of 1-napthyl, 2-napthyl, 2-furyl, 3-furyl, 2-thienyl, 2-pyridyl, 3-pyridyl, 4-pyridyl and phenyl having 1-3 substituent(s) independently selected from the group consisting of hydrogen, halo, hydroxy, nitro, $CF_3$, $C_1$–$C_6$ straight or branched chain alkyl, $C_2$–$C_6$ straight or branched chain alkenyl, O—($C_1$–$C_4$ straight or branched chain alkyl), O—($C_2$–$C_4$ straight or branched chain alkenyl), O-benzyl, O-phenyl, amino, and phenyl.

D is hydrogen or U; E is oxygen or CH—U, provided that if D is hydrogen, then E is CH—U, or if E is oxygen, then D is U;

U is hydrogen, O—($C_1$–$C_4$ straight or branched chain alkyl), O-($C_2$–$C_4$ straight or branched chain alkenyl), $C_1$–$C_6$ straight or branched chain alkyl, $C_2$–$C_6$ straight or branched chain alkenyl, $C_5$–$C_7$-cycloalkyl, $C_5$–$C_7$ cycloalkenyl substituted with $C_1$–$C_4$ straight or branched chain alkyl or $C_2$–$C_4$ straight or branched chain alkenyl, 2-indolyl, 3-indolyl, ($C_1$–$C_4$ alkyl or $C_2$–$C_4$ alkenyl)-Ar, or Ar;

J is hydrogen, $C_1$ or $C_2$ alkyl, or benzyl; K is $C_1$–$C_4$ straight or branched chain alkyl, benzyl or cyclohexylethyl; or J and K are taken together to form a 7 membered heterocyclic ring which is substituted with oxygen, sulfur, SO, or $SO_2$; and said compound has an affinity for FKBP-type immunophilins.

3. A method for treating alopecia or promoting hair growth in an animal in need thereof, which comprises administering to said animal an effective amount of a compound of formula IV

IV or a pharmaceutically acceptable salt, ester, or solvate thereof, wherein:

V is C, N, or S;

J and K, taken together with V and the carbon atom to which they are respectively attached, form a 7 membered saturated or unsaturated heterocyclic ring having, in addition to V, one or more heteroatom(s) selected from the group consisting of O, S, SO, $SO_2$, N, NH, and NR;

R is either $C_1$–$C_9$ straight or branched chain alkyl, $C_2$–$C_9$ straight or branched chain alkenyl, $C_3$–$C_9$ cycloakyl, $C_5$–$C_7$ cycloalkenyl, or $Ar_1$, wherein R is either unsubstituted of substituted with one or more substituent(s) independently selected from the group consisting of halo, haloalkyl, carbonyl, carboxy, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, thioalkyl, alkylthio, sulfhydryl, amino, alkylamino, aminoalkyl, aminocarboxyl, and $Ar_2$;

$Ar_1$ and $Ar_2$ are independently an alicyclic or aromatic, mono-, bi- or tricyclic, carbo- or heterocyclic ring; wherein the individual ring size is 5–8 members; wherein said heterocyclic ring has 1–6 heteroatom(s) independently selected from the group consisting of O, N, and S;

A is O, NH, or N—($C_1$–$C_4$ alkyl);

B and D are independently Ar, $C_5$–$C_7$ cycloalkyl substituted $C_1$–$C_6$ straight or branched chain alkyl or $C_2$–$C_6$ straight or branched chain alkenyl, $C_5$–$C_7$ cycloalkenyl substituted $C_1$–$C_6$ straight or branched chain alkyl or $C_2$–$C_6$ straight or branched chain alkenyl, or Ar substituted $C_1$–$C_6$ straight or branched chain alkyl or $C_2$–$C_6$ straight or branched chain alkenyl, wherein in each case, one or two carbon atom(s) of said alkyl or alkenyl is/are optionally substituted with one or two heteroatom(s) independently selected from the group consisting of oxygen, sulfur, SO, and $SO_2$, or wherein O is hydrogen, $C_1$–$C_6$ straight or branched chain alkyl or $C_2$–$C_6$ straight or branched chain alkenyl; and T is Ar or $C_5$–$C_7$ cycloalkyl substituted at positions 3 and 4 with substituents independently selected from the group consisting of hydrogen, hydroxy, O—($C_1$–$C_4$ alkyl), O—($C_2$–$C_4$ alkenyl), and carbonyl;

Ar is selected from the group consisting of 1-napthyl, 2-napthyl, 2-furyl, 3-furyl, 2-thienyl, 3-thienyl, 2-pyridyl, 3-pyridyl, 4-pyridyl and phenyl, monocyclic and bicyclic heterocyclic ring systems with individual ring sizes being 5 or 6 which have in either or both rings a total of 1–4 heteroatoms independently selected from oxygen, nitrogen and sulfur; wherein Ar has 1–3 substituent(s) independently selected from the group consisting of hydrogen, halo, hydroxy, hydroxymethyl, nitro, $CF_3$, trifluoromethoxy, $C_1$–$C_6$ straight or branched chain alkyl, $C_2$–$C_6$ straight or branched chain alkenyl, O—($C_1C_4$ straight or branched chain alkyl), O—($C_2$–$C_4$ straight or branched chain alkenyl), O-benzyl, O-phenyl, amino, 1,2-methylenedioxy, carbonyl, and phenyl;

L is either hydrogen or U; M is either oxygen or CH—U, provided that if L is hydrogen, then M is CH—U, or if M is oxygen then L is U;

U is hydrogen, O—($C_1$–$C_4$ straight or branched chain alkyl), O—($C_2$–$C_4$ straight or branched chain alkenyl), $C_1$–$C_6$ straight or branched chain alkyl, $C_2$–$C_6$ straight or branched chain alkenyl, $C_5$–$C_7$ cycloalkyl, $C_5$–$C_7$ cycloalkenyl substituted with $C_1$–$C_4$ straight or branched chain alkyl or $C_2$–$C_4$ straight or branched chain alkenyl, ($C_1$–$C_4$ alkyl or $C_2$–$C_4$ alkenyl)-Ar, or Ar;

m is 0–3; and said compound has an affinity for FKBP-type immunophilins.

* * * * *